United States Patent [19]

Fields

[11] 4,432,847
[45] Feb. 21, 1984

[54] POLY SULFOXIDES FROM 1,3,4-THIADIAZOLE-2,5-DITHIOL

[75] Inventor: Ellis K. Fields, River Forest, Ill.

[73] Assignee: Standard Oil Company (Indiana), Chicago, Ill.

[21] Appl. No.: 709,780

[22] Filed: Jul. 29, 1976

[51] Int. Cl.³ .................. C07D 285/12; C07D 417/12; C07D 417/14

[52] U.S. Cl. .............................. 204/158 R; 252/47.5; 252/391; 252/394; 546/148; 546/172; 546/277; 548/142; 424/258; 424/263; 424/270

[58] Field of Search .................. 260/302 SD, 294.8 D; 204/158, 158 R, 158 N, 158 T; 548/142; 546/277

[56] References Cited

U.S. PATENT DOCUMENTS 3,753,999  8/1973  Tempel et al. ............ 260/302 SD

FOREIGN PATENT DOCUMENTS 1568552  5/1969  France .................. 260/302 SD

Primary Examiner—Alton D. Rollins
Attorney, Agent, or Firm—William C. Clarke; William T. McClain; William H. Magidson

[57] ABSTRACT

Poly sulfoxides of the general formula

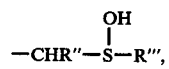

where each R is a monovalent aliphatic radical bound to a sulfoxy group. Each R is defined as being individually selected from the group consisting of —R′, —CHR″—S(=O)—R‴, —CHR″—S—R‴, and

—CHR″—S(OH)—R‴, wherein R′, R″ and R‴ are individually selected from the group consisting of alkyl moieties containing 1 to 22 carbon atoms, and aralkyl moieties, alkylated aryl moieties, heterocyclic alkyl moieties, cycloalkyl moieties containing 4 to 40 carbon atoms wherein the said moieties are joined to the sulfoxy group through the alkyl chain, the said moieties being unsubstituted and substituted, said substitutions being individually selected from the group consisting of halogen moieties, nitro moieties, alkoxy moieties, alkyl moieties, and dialkylamino moieties.

19 Claims, No Drawings

POLY SULFOXIDES FROM 1,3,4-THIADIAZOLE-2,5-DITHIOL

BACKGROUND OF THE INVENTION

The field of this invention relates to novel compositions of matter which are poly sulfoxides. These compounds are prepared by selective oxidation of thioethers, namely, 2,5-alkylthio-1,3,4-thiadiazoles. These novel compounds are surface active agents suitable for surfactants, have rust inhibiting properties and biocidal activity.

Organic sulfur compounds are of considerable industrial importance. Novel organic sulfur compounds with characteristics suitable for use in soluble oil compositions, tertiary oil recovery micellar fluids and miscellaneous uses such as pesticides are of extensive utility. For example, steam turbine and other industrial oils can be stabilized against the rusting of ferrous parts should water become mixed with the oil. An important use of soluble oils is as lubricating and cooling agents in the cold working of metals such as in grinding, cutting and threading operations. For this use, the soluble oil is dispersed in from about 10 to 80 or more times its own volume of water and circulated over the contact point of the working tool and the metal being worked on. Frequently, difficulty is encountered in this type of operation due to the tendency of the soluble oil emulsion or dispersion to cause rusting of metals in contact with such emulsions, particularly ferrous metals and also because in the course of time, these emulsions or dispersions develop strong, putrid, undesirable odors if the soluble oil composition does not contain a bactericide.

DESCRIPTION OF THE PRIOR ART

This invention relates to bis sulfoxides and more particularly to 1,3,4-thiadiazole-2,5-di-, tri-, tetrasulfoxides and 1,3,4-thiadiazole-2,5-β-hydroxysulfoxides, their preparation and their use as surface active agents, rust inhibitors and biocides.

A number of bis sulfoxides have been prepared. Among them are bis-2-acetoxyphenylsulfoxide (W. S. Gump et. al., *J. Amer. Chem. Soc.*, 67, 238 (1945)), bis-2-hydroxyethylsulfoxide (A. H. Ford-More, *J. Chem. Soc.*, 2126 (1949)), and bis(2-nitro-4-trifluoromethylphenyl)sulfoxide (N. K. Kharasch, *Organic Sulfur Compounds I*, Pergamon, New York, 161 (1961)). However, poly sulfoxides containing a 1,3,4-thiadiazole moiety with the sulfoxide groups attached in the 2,5-positions have not been previously known.

The preparation of sulfoxides in the prior art has been through the oxidation of sulfides using (a) peroxides, peracids and ozone, (b) chromic acid, (c) nitric acid and oxides of nitrogen, (d) iodosobenzene and derivatives, and (e) some miscellaneous methods such as using manganese dioxide, lead tetraacetate, potassium permanganate, etc.

The novel composition of matter of my invention are provided by the above methods and by use of actinic radiation in the presence of oxygen. The 1,3,4-thiadiazole-2,5-di-, tri-, tetrasulfoxides are prepared by the oxidation of sulfides. The bis-1,3,4-thiadiazole-2,5-β-hydroxysulfoxides are prepared by use of molecular oxygen and actinic radiation in the presence of a dye sensitizer. These compositions of matter can be used to prevent rusting of iron chips in water, prevent the growth of fungi and bacteria, and can be used as surface-active agents.

Although 1,3,4-thiadiazole-2,5-sulfoxides and bis-1,3,4-thiadiazole-2,5-β-hydroxylsulfoxides have not been previously prepared, 1,3,4-thioethers of 1,3,4-thiadiazole-2,5-dithiol (DMTD) have been prepared and their properties are known. Thioethers have been made either by alkylation of sodium or potassium salts of 1,3,4-thiadiazole-2,5-dithiol with alkyl halides, where the halogen is bromine, chlorine or iodine or by reaction of 1,3,4-thiadiazole-2,5-dithiol with two or more moles of an olefin, Bambas, L. L. *Chemistry of Heterocyclic Compounds*, IV, 177–98, Interscience, N. Y., (1952). Other thioethers have been prepared by condensation of 2,5-dimercaptothiadiazole with hydroxymethylphenols.

I have prepared thioacetals, a type of thioether, by warming equimolar quantities of aldehyde and 2,5-dimercaptothiadiazole, as is disclosed in my previous publication, *Ind. Eng. Chem.*, 49, 1361 (1957). I also reported preparation of mixed thioacetals without catalysts from formaldehyde or other aldehydes and mercaptans.

However, there has not been a disclosure where a thioether was oxidized to form a sulfoxide compound from a 1,3,4-thiadiazole-2,5-dithiol. More specifically, the preparation of 1,3,4-thiadiazole-2,5-di-, tri-, and tetrasulfoxides and β-hydroxysulfoxides has not been suggested.

SUMMARY OF THE INVENTION

Novel poly sulfoxide compounds are prepared by selective oxidation of 2,5-alkylthio-1,3,4-thiadiazoles which can be substituted with carbon chains and/or carbon groups of up to 40 carbon atoms which, in turn, can be substituted with halogens, nitro, alkoxy and dialkylamino groups. These sulfoxides are useful as surfactants, rust inhibitors and biocides. These thiadiazoles are oxidized to these novel poly sulfoxides in a liquid phase oxidation at a temperature within the range of 0° to 40° C., the oxidizing agent selected from the group consisting of hydrogen peroxide or molecular oxygen.

DETAILED DESCRIPTION OF INVENTION

Poly sulfoxides of the general formula

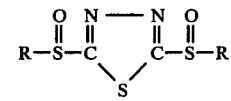

where each R is a monovalent aliphatic radical bound to a sulfoxy group. Each R is defined as being selected from the group consisting of

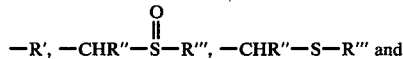

wherein R′, R″ and R′″ are individually selected from the group consisting of hydrogen, alkyl moieties containing 1 to 22 carbon atoms, and aralkyl moieties, alkylated aryl moieties, heterocyclic alkyl moieties, cycloalkyl moieties containing 4 to 40 carbon atoms wherein the said moieties are joined to the sulfoxy group through the alkyl chain, the said moieties being unsubstituted and substituted, said substitutions being individually selected from the group consisting of halogen moieties, nitro moieties, alkoxy moieties, alkyl moieties, and dialkylamino moieties.

The di-, tri- and tetrasulfoxides of this invention have the following structures, namely:

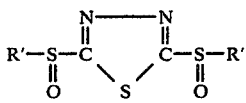

(1) a disulfoxide

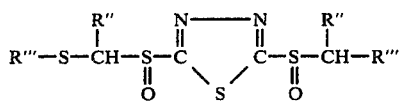

and
(2), also a disulfoxide,

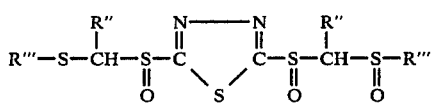

(3) a trisulfoxide,

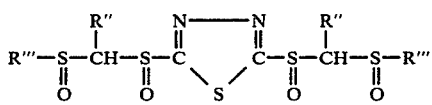

and
(4), a tetrasulfoxide.

The bis-β-hydroxysulfoxides of this invention have the structure:

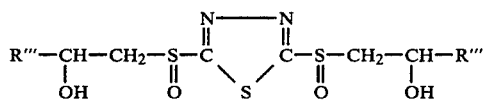

R', R" and R''' have the significance as given above.
Typical compounds of this invention include:

2,5-bis(2-octylsulfoxy)-1,3,4-thiadiazole
2,5-bis(2-dodecylsulfoxy)-1,3,4-thiadiazole
2,5-bis(methylsulfoxy)-1,3,4-thiadiazole
2,5-bis(1-t-octylthiomethylsulfoxy)-1,3,4-thiadiazole
2-(1-t-octylthiomethylsulfoxy)-5-(1-t-octylsulfoxymethylsulfoxy)-1,3,4-thiadiazole
2,5-bis(1-t-octylsulfoxymethylsulfoxy)-1,3,4-thiadiazole
2,5-bis(1-t-dodecylthiomethylsulfoxy)-1,3,4-thiadiazole
2,5-bis(1-t-dodecylsulfoxymethylsulfoxy)-1,3,4-thiadiazole
2,5-bis(1-t-hexadecylthiomethylsulfoxy)-1,3,4-thiadiazole
2-(1-t-hexadecylthiomethylsulfoxy)-5-(1-t-hexadecylsulfoxymethylsulfoxy)-1,3,4-thiadiazole
2,5-bis(1-t-hexadecylsulfoxymethylsulfoxy)-1,3,4-thiadiazole
2,5-bis(1-t-hexadecylthiomethylphenylsulfoxy)-1,3,4-thiadiazole
2,5-bis(1-t-hexadecylsulfoxymethylphenylsulfoxy)-1,3,4-thiadiazole
2,5-bis(1-t-hexadecylthio-1-hexylmethylsulfoxy)-1,3,4-thiadiazole
2,5-bis(1-t-hexadecylsulfoxy-1-hexylmethylsulfoxy)-1,3,4-thiadiazole
2,5-bis(1-octylthiomethylsulfoxy)-1,3,4-thiadiazole
2,5-bis(1-octylsulfoxymethylsulfoxy)-1,3,4-thiadiazole
2,5-bis(β-hydroxy-β-phenylethylsulfoxy)-1,3,4-thiadiazole
2,5-bis(β-hydroxyoctyl-4-sulfoxy)-1,3,4-thiadiazole
2,5-bis(β-hydroxydodecylsulfoxy)-1,3,4-thiadiazole
2,5-bis(β-hydroxy-β,4-pyridylethylsulfoxy)-1,3,4-thiadiazole
2,5-bis(β-hydroxy-β,2-pyridylethylsulfoxy)-1,3,4-thiadiazole The novel sulfoxide compounds derived from 1,3,4-thiadiazole-2,5-dithiol, commonly named 2,5-dimercaptothiadiazole or DMTD, which are the subject of my invention, can be summarized as being a class of oxidized thioether derivatives of DMTD, the particular member of the class being dependent upon whether the DMTD is in the form of a thioacetal when it is reacted to form a thioether and the form of oxidizing agent utilized upon the resultant thioether. If hydrogen peroxide or another oxidizing agent is used such as m-chloroperbenzoic acid, peracetic acid, performic acid, or tert-butyl hydroperoxide catalyzed by molybdenum or other transition metal ion, the resultant compounds are bis sulfoxides. If molecular oxygen and actinic radiation, such as ultraviolet and visible light, in the presence of a dye sensitizer is used, the resulting compound is a bis hydroxy sulfoxide.

For purposes of this invention, the term "bis" is defined, as in the Condensed Chemical Dictionary, 8th Ed., Reinhold, 1971, as indicating a chemical grouping or radical occurs twice in a molecule, or as in Hackh's Chemical Dictionary, "bis" indicates twice and is generally applied to molecules made up of two similar halves. The term "alkyl moiety" is defined as including monovalent chain saturated hydrocarbon groups containing 1 to 22 carbon atoms, i.e., methyl, ethyl, propyl, isopropyl, butyl and isobutyl, 2-ethylhexyl, amyl, hexyl, heptyl, dodecyl, octyl, isotridecyl, stearyl, oleyl, and tetracosyl groups. The term "aralkyl moiety" is defined as including groups composed of monovalent chain saturated hydrocarbon moieties containing from 1 to 22 carbon atoms attached to aromatic moieties containing 6 to 18 carbon atoms such as phenyl, biphenyl, naphthyl, anthranyl, etc. The term "alkylated aryl moieties" is defined as including aromatic moieties containing 6 to 18 carbon atoms, i.e., phenyl, biphenyl, naphthyl, anthranyl, etc., the said aromatic moieties being substituted with alkyl groups up to ten in number, the said alkyl groups containing from one to four carbon atoms. The term "heterocyclic alkyl moieties" is defined as a group containing a cyclic or ring structure of five or more atoms in the ring in which one or more atoms in the ring is an element other than carbon and can be oxygen, nitrogen and/or sulfur, the ring structure attached to an alkyl group containing one to 22 carbon atoms, the said ring structure containing up to three cyclic analogues. Examples are thienyl, pyridyl, benzothienyl, thienobenzenyl, quinolyl, isoquinolyl, dibenzothienyl and phenanthridyl groups. The term "cycloalkyl moieties" is defined as including saturated cyclic moieties such as the monocyclic groups cyclohexyl, cycloheptyl, cyclooctyl, the dicyclic groups and the tricyclic groups such as decahydronaphthalene (decalin), perhydroanthracene and perhydrophenanthrene containing up to 40 carbon atoms. The above same groups can be substituted or unsubstituted, containing such substituents such as halogens (fluorine, chlorine, bromine and iodine), nitro and alkyl groups, alkoxy groups such as methoxy, ethoxy, propoxy, butoxy, decyloxy and dodecyloxy groups. Examples of these several groups and moieties are given in the discussion of the starting compounds.

Selective oxidation of the 2,5-alkylthiol-1,3,4-thiadiazoles to the poly sulfoxides of my invention can be by any of the usual oxidizing agents such as chloroperbenzoic acid, peracetic acid, performic acid, or butyl hydroperoxide catalyzed by molybdenum or other transition metal ion. A convenient method is by means of a solution of 5–50% of 30% aqueous hydrogen peroxide in acetic acid; preferred is 10–30% by weight of the aqueous hydrogen peroxide at mole ratios of 1.7–4 of hydrogen peroxide per mole of starting compound at 0° to 40° C. for 0.5 to 48 hours. Preferred conditions are 10°–25° C. for 2–24 hours.

The novel bis-(beta-hydroxysulfoxides) can be obtained by a selective oxidation reaction of the sulfide using molecular oxygen and actinic radiation, which can be ultraviolet light or visible light, in the presence of a dye sensitizer. If visible light is used, the dye sensitizer can be selected from the group consisting of methylene blue, Eosin, and Rose Bengal. Ketones in general, such as acetone, can also act as sensitizers.

In general, the reaction with molecular oxygen is carried out with an olefin-thiadiazole dithiol mixture wherein the ratio can be from 2:1 to 5:1, preferred ratio is 2:1 to 2.2:1. Reactions are run in a solvent such as dioxane, acetone, or ether at 10° to 40° C. under oxygen at 5 to 200 psig for 0.5 to 150 hours. Preferred conditions are 20° to 25° C. under oxygen at 15 to 30 psig for 2 to 30 hours. The reaction below 10° C. tends to be very slow. As the temperature is increased above the range from about 10° to 40° C., there is a tendency for the sulfide to decompose under the conditions of the reaction. A dye such as methylene blue, or Rose Bengal in acetone solution is added to give concentrations of 0.0001 to 0.1% by weight; preferred is 0.005 to 0.05% by weight. A convenient method of running the reactions is by shaking the reaction mixture in a pressure bottle in a Parr Pressure Reaction Apparatus under illumination from the source of actinic radiation (visible or ultraviolet light) such as a photoflood lamp, a sun lamp, or a 300–500 watt light bulb in a reflector. The reaction is continued until the absorption of oxygen slows or ceases. The filtered solutions are evaporated in a Rotovapor apparatus at 30° to 40° C. under 0.01 to 1 mm pressure.

In general, the sulfides, from which the sulfoxides are derived, are prepared by one of three procedures. In the first procedure, the unoxidized starting compounds can be prepared by reacting the sodium or potassium salt of 1,3,4-thiadiazole-2,5-dithiol with halo compounds RX and R'X. R and R' can be the same or different straight or branched chain alkyl groups containing 1 to 22 carbon atoms, preferably 4 to 18 carbon atoms; aralkyl groups, alkylated aryl groups, heterocyclic alkyl groups, cyclo alkyl groups, the last four containing 4 to 40 carbon atoms, preferably 6 to 24 carbon atoms, and the same groups containing substituents such as halogen, nitro, alkoxy or dialkylamino groups. Examples of these compounds are n-butyl chloride, n-hexyl iodide, isobutyl bromide, n-dodecyl bromide, isostearyl iodide, benzyl chloride, p-methylbenzyl bromide, β-phenethyl bromide, α-chloromethyl naphthalene, 4-chloro-1-iodobutane, β-nitrobutyl bromide, 3-methoxy-butyl chloride, 1-diethylamino-ethyl chloride, 4-nitrobenzyl chloride, 4-chlorobenzyl chloride, 4-chloromethyl anisole, 4-diethylaminobenzyl chloride, 2-chloromethyl furan, 3-chloromethyl thiophene, 4-chloromethylpicoline, cyclohexyl bromide, 1-fluoro-4-bromocyclohexane, 2-methoxy cyclopentyl chloride, 6-nitro-2-chloromethyl quinoline, and 6-diethylamino-2-chloromethyl isoquinoline.

A second method, which I have used and described in *J. Org. Chem.*, 21, 497 (1956), consists of heating together 1,3,4-thiadiazole-2,5-dithiol with one or more moles of an olefinically unsaturated compound of the structure R—CH=CHR', wherein R and R' have same significance as given above, at 50°–150° C. for 1 to 165 hours.

The olefinically unsaturated compound employed in the olefinic method can be an aliphatic, aromatic, or heterocyclic olefin of the characteristics as given above; however, preferred are olefins where R' is H, and the olefin is R—CH=CH$_2$. Representative olefinically unsaturated compounds that can be used as exemplary of the reaction are styrene, alpha-methylstyrene, alpha-p-dimethylstyrene, allylbenzene, cyclohexene, 1-vinylcyclohexane, ethylene, propylene, 1-butene, 1-octene, 1-dodecene, 1-octadecene, 2 and 4-vinyl-pyridine, 2-vinylthiophene, 4-chlorostyrene, 4-nitrostyrene, eugenol methyl ether, and 4-dimethylamino styrene.

In preparing the starting compounds by means of the olefinic procedure, the adducts were prepared by stirring 1,3,4-thiadiazole-2,5-dithiol (DMTD) with an olefin at 110°–130° C. until all the solid had disappeared. When one mole of olefin was used per mole of DMTD, the mixture was stirred for one additional hour; with two moles of olefin, for 10–24 hours. When ratio was greater than 2 to 1, the mixture was stirred for up to 165 hours. A solvent was utilized when needed, the solvent being selected from the group consisting of benzene, dioxane or any other suitable hydrocarbon or oxygen-containing solvent. All crystalline adducts were recrystallized from benzene or petroleum ether.

The non-crystalline 1:1 adducts, which had an acidic SH group, were purified by dissolving in excess 10% sodium carbonate solution, separating the aqueous solution and acidifying with dilute hydrochloric acid. The liberated oils were separated, dried and filtered. Traces of moisture were removed by heating under a vacuum at 80° C.

The 1:2 adducts, all viscous oils or glasses, were purified by being diluted with ether, extracted with sodium hydroxide solution, washed with water, dried and evaporated under a vacuum at 80°–90° C. and 0.2 Torr.

The starting compounds can be prepared in a third method by reacting aldehydes of structure R—CHO with 1,3,4-thiadiazole-2,5-dithiol and thiols of structure R'—SH where R and R' have the same significance as described previously in the ratio of 2:1:2 at 80° C. Reference is made to my U.S. Pat. No. 2,703,785 to E. K. Fields, which is incorporated by reference.

The aldehyde employed in the carbonyl method can be an aliphatic, an aromatic, or a heterocyclic aldehyde of from about 1 to 22 or more carbon atoms, and can contain substituents, such as alkoxy, hydroxy, alkyl mercapto, halogen, or nitro groups. Ketones can also be used. Examples of suitable aldehydes are formaldehyde, acetaldehyde, benzaldehyde, 2-ethylhexyl aldehyde, butyraldehyde, heptaldehyde, caprylic aldehyde, acrylicaldehyde, crotonaldehyde, vinyl acetaldehyde, phenyl acetaldehyde, nitrobenzaldehyde, salicylaldehyde, furfural, chloral, etc. Of the aldehydes, the aliphatic aldehydes, particularly the low molecular weight aldehydes, such as formaldehyde, are preferred. Examples of suitable ketones are acetone, 2-butanone, 2-acetofuran, furyl methyl ketone, acetophenone, 1,1,1-trifluoroacetone, 3-nitroacetophenone, 4-hydroxy-2-butanone, methyl-3-pyridyl ketone, 3-methylthioacetophenone, acetyl cyclohexane, dicyclopentyl ketone.

In general, in the exercise of the carbonyl method of preparation, the reaction is carried out by adding an aldehyde or ketone to a mixture of the mercaptan and the thiadiazole-dithiol (which is DMTD), and heating the mixture at a temperature of from about 40° C. to about 140° C. for a period of from about 20 minutes to about 16 hours. Preferably, the reaction is carried out in the presence of a suitable solvent, such as by way of example, dioxane, ethylene glycol dimethyl and diethyl ethers, and diethylene glycol dimethyl and diethyl ethers. At the end of the reaction, the solvent and the water produced in the reaction are removed from the reaction product, preferably by stripping in a vacuum, and the stripped product filtered if necessary.

Any mercaptan can be employed in the carbonyl method of preparation, although aliphatic and aromatic mono- or polymercaptans containing from about 1 to about 40 carbon atoms, and preferably from about 6 to 20 carbon atoms, are preferred. For bacteria growth control, better results are usually obtained with aliphatic mercaptans of from about 8 to 12 carbon atoms. Examples of suitable mercaptans are ethyl mercaptan, butyl mercaptan, hexyl mercaptan, octyl mercaptan, nonyl mercaptan, octadecyl mercaptan, thiophenol, etc.

Although the herein described thiadiazole derivatives all exhibit to a definite degree anti-rust properties, surfactant properties, and bacteria growth control properties, all are not necessarily equivalent in their effectiveness, since, depending upon the nature and severity of the service in which they are used, some variation in effectiveness may be exhibited.

In summary, the invention consists of a family of poly sulfoxides which are prepared by the selective oxidation of thioethers selected from the group consisting of 2,5-alkylthio-1,3,4-thiadiazoles and mixed thioacetals of 1,3,4-thiadiazole-2,5-dithiol (DMTD) wherein the alkyl moiety of said thiadiazoles is selected from the group consisting of methyl, ethyl, proxyl, isopropyl, butyl, isobutyl, 2-ethylhexyl, amyl, hexyl, heptyl, dodecyl, octyl, isotridecyl, stearyl, oleyl, tetracosyl moieties, the said alkyl moiety being terminated by a group selected from the group consisting of hydrogen, phenyl, biphenyl, naphthyl, anthranyl, thienyl, pyridyl, benzothienyl, thienobenzenyl, quinolyl, isoquinolyl, dibenzothienyl, phenanthridyl, cyclohexyl, cycloheptyl, cyclooctyl, decahydronaphthalene, perhydroanthracene, perhydrophenanthrene radicals, said radicals when substituted, being substituted with substituents selected from the group of substituents consisting of fluorine, chlorine, bromine, iodine, nitro, methoxy, ethoxy, propoxy, butoxy, decyloxy and dodecyloxy substituents. The mixed thioacetals are prepared by reacting aldehydes or ketones with 1,3,4-thiadiazole-2,5-dithiol and thiols of structure R'SH wherein R' has the same description as the alkyl moiety of the above 2,5-alkylthio-1,3,4-thiadiazoles. Examples of suitable aldehydes are formaldehyde, acetaldehyde, benzaldehyde, 2-ethylhexyl aldehyde, butyraldehyde, heptaldehyde, caprylic aldehyde, acrylicaldehyde, crotonaldehyde, vinyl acetaldehyde, phenylacetaldehyde, nitrobenzaldehyde, salicylaldehyde, furfural, chloral, etc. Examples of suitable ketones are acetone, 2-butanone, 2-acetofuran, furyl methyl ketone, acetophenane, 1,1,1-trifluoroacetone, 3-nitroacetophenane, 4-hydroxy-2-butane, methyl-3-pyridyl ketone, 2-methylacetophenone, acetyl cyclohexane, dicyclopentyl ketone. Examples of suitable thiols are ethyl mercaptan, butyl mercaptan, hexyl mercaptan, octyl mercaptan, nonyl mercaptan, octadecyl mercaptan, thiophenol, etc.

The invention also consists of the preparation of bis beta hydroxy sulfoxides using molecular oxygen with actinic radiation such as visible light in the presence of a dye sensitizer.

The preparation of the above-described reaction products is illustrated by the following examples, which are given by way of illustration and are not intended to limit the scope of the invention.

The following examples illustrate the preparation of a bis-disulfoxide using an olefin and DMTD.

EXAMPLE I

A solution of 19.85 g (0.0545 mole) of dioctylthiothiadiazole prepared as described below was stirred in 50 ml of acetic acid in a 3-necked round-bottom flask equipped with a thermometer, a reflux condenser, a dropping funnel, and a magnetic stirrer. The solution was maintained at below 30° C. by cooling while 8.67 ml (0.11 mole) of 30% aqueous hydrogen peroxide were added dropwise over 1 hour. The reaction mixture was stirred at 25° C. for 12 hours, then evaporated in a Rinco evaporator at 30°-35° C. and 0.2 Torr. The product was a viscous, light-brown oil; 21.4 g (99 mole % yield), 2,5-bis(2-octylsulfoxy)-1,3,4-thiadiazole.

Analysis: Calcd. for $C_{18}H_{34}N_2S_3O_2$—C, 55.4%; H, 8.7%; N, 7.2%; S, 24.6%. Found: C, 55.3%; H, 8.6%; N, 7.1%, S, 24.3%.

The thiadiazole used was prepared as follows:

A mixture of 30 g (0.2 mole) of 1,3,4-thiadiazole-2,5-dithiol and 77.6 ml (0.5 mole) of 1-octene was stirred and refluxed for 165 hours at a pot temperature of 122° C. in a 3-necked round-bottom flask equipped with a thermometer, a reflux condenser, a dropping funnel, and a magnetic stirrer. The cooled mixture was diluted with 300 ml. of ether, extracted with 2 portions of 100 ml 1 N sodium hydroxide, washed with water, dried, and evaporated in a Rinco evaporator, (Rotovapor) at 80°-90° C. and 0.2 Torr. The residue, a viscous yellow oil, consisted of bis-2,5-(2-n-octylthio)-1,3,4-thiadiazole.

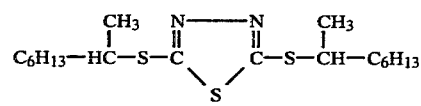

Analysis Calcd. for $C_{18}H_{34}N_2S_3$—C, 57.8%; H, 9.1%; N, 7.5%; S, 25.7%. Found: C, 57.6%; H, 9.0%; N, 7.7%; S, 25.4%.

Acidification of the sodium hydroxide extract yielded 20.6 g of 2-octylthio-1,3,4-thiadiazole-5-thiol, the monoadduct of 1-octene; 23 ml of 1-octene were recovered.

EXAMPLE II

A solution of 26.2 g (0.054 mole) of the bis dodecylthiothiadiazole prepared as below was stirred, according to the procedure of Example I, in 50 ml of acetic acid and 50 ml of benzene. While the temperature was maintained below 30° C., 9.5 ml. (0.12 mole) of 30% hydrogen peroxide were added dropwise over 1 hour. Stirring was continued for 24 hours at 25° C. The mixture was evaporated in a Rinco evaporator at 40° C. and 0.2 Torr. to give 24.2 g (87 mole % yield) of disulfoxide, 2,5-bis(2-dodecylsulfoxy)-1,3,4-thiadiazole.

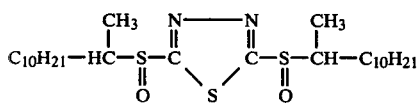

Analysis: Calculated—C, 60.2%; H, 9.7%; N, 5.4%; S, 18.5%. Found: C, 60.2%; H, 9.4%; N, 5.5%; S, 18.8%.

Preparation of the thiadiazole was as follows:

A mixture of 15 g (0.1 mole) of 1,3,4-thiadiazole-2,5-dithiol, 29.15 ml (0.22 mole) of 1-dodecene, and 25 ml of dioxane was stirred at 100° C. using the procedure of Example I. A clear solution formed in 30 minutes. Heating at 100° C. was continued for 72 hours. The cooled mixture was diluted with 350 ml of ether, the ether solution was extracted with 2 150 ml portions of 1 N sodium hydroxide, then washed with water, dried, and evaporated in a Rinco evaporator at 80° C. and 0.2 Torr. to give as residue, a light-brown viscous oil, 26.2 g.

Analysis: Calcd. for

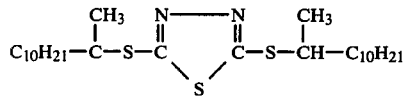

C, 64.2%; H, 10.3%; N, 5.7%; S, 19.8%. Found: C, 63.9%; H, 10.1%; N, 5.9%; S, 20.0%.

EXAMPLE III

A solution of 8.9 g (0.05 mole) of 2,5-dimethylthio-1,3,4-thiadiazole product (prepared as described below) in 50 ml of acetic acid was treated with 7.48 ml (0.1 mole) of 30% aqueous hydrogen peroxide at 20°-25° C. The mixture was stirred at 25° C. for 18 hours according to the procedure of Example I, then evaporated in a Rotovapor to obtain 10.3 g (98 mole % yield) of the disulfoxide, 2,5-bis(methylsulfoxy)-1,3,4-thiadiazole.

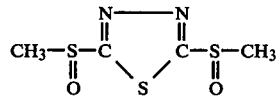

Analysis: Calcd. for $C_4H_6N_2S_3O_2$—C, 22.9%; H, 2.9%; N, 13.3%; S, 45.7%. Found: C, 22.8%; H, 3.1%; N, 13.6%; S, 45.8%.

To prepare the above thiadiazole, a solution of 30 g (0.2 mole) of 1,3,4-thiadiazole-2,5-dithiol and 22.4 g (0.4 mole) of potassium hydroxide in 300 ml of methanol was treated with 20.9 ml (0.4 mole) of methyl iodide. The mixture was stirred and refluxed according to the procedure of Example I for 10 hours, cooled, filtered from potassium iodide, and distilled to obtain 29 g (81.5 mole % yield) of 2,5-dimethylthio-1,3,4-thiadiazole boiling at 85°-87° C. at 0.15 Torr.

EXAMPLES IV-XXIII

The following Examples IV throught XXIII are examples of the products from the reaction of 1,3,4-thiadiazole-2,5-dithiol (DMTD) with aldehydes RCHO and thiols R'—SH.

In the Examples IV through IX given in Table I, the reagents, 1,3,4-thiadiazole-2,5-dithiol and thiol in 200 to 300 milliliters of dioxane, were stirred at 70° to 80° while the aldehyde was added dropwise over 20 to 30 minutes. The mixture within was refluxed 2 hours, cooled, and evaporated in a Rotovapor rotary evaporator at 60° to 70° C. and 0.1 to 0.2 Torr. to give the products shown in Table I.

TABLE I

Products From the Reaction of 1,3,4-Thiadiazole-2,5-Dithiol (DMTD) With Aldehydes R—CH=O And Thiols R'SH

| Example | DMTD Grams, Moles | Aldehyde R =, Ml., Moles | Thiol R' =, Ml., Moles | Wt. of Product, Grams |
|---|---|---|---|---|
| IV | 30, 0.2 | H, 33 of 36% 0.4 | Tert-octyl, 68, 0.4 | 67.7 |
| V | 30, 0.2 | H, 33 of 36%, 0.4 | Tert-dodecyl, 95, 0.4 | 112.3 |
| VI | 30, 0.2 | H, 33 of 36%, 0.4 | Tert-hexadecyl, 120, 0.4 | 134.4 |
| VII | 30, 0.2 | Phenyl, 40.5, 0.4 | Tert-hexadecyl, 120, 0.4 | 109.6 |
| VIII | 30, 0.2 | n-hexyl, 55.9, 0.4 | Tert-hexadecyl, 120, 0.4 | 155.3 |
| IX | 15, 0.1 | H 16.5 of 36% 0.2 | n-octyl, 36, 0.2 | 52.3 |

Analyses of the products of Examples IV to IX are shown in Table II.

TABLE II

Elemental Analyses of Products of Examples VII to XII

| Product of Example # | C Fd. | C Calcd. | H Fd. | H Calcd. | N Fd. | N Calcd. | S Fd. | S Calcd. |
|---|---|---|---|---|---|---|---|---|
| IV $C_{20}H_{38}N_2S_5$ | 51.4 | 51.5 | 8.4 | 8.2 | 5.7 | 6.0 | 33.8 | 34.3 |
| V $C_{28}H_{54}N_2S_5$ | 58.3 | 58.1 | 9.3 | 9.3 | 4.5 | 4.8 | 28.3 | 27.7 |
| VI $C_{36}H_{70}N_2S_5$ | 63.0 | 62.6 | 9.9 | 10.1 | 4.1 | 4.1 | 23.0 | 23.2 |
| VII $C_{48}H_{78}N_2S_5$ | 69.1 | 68.4 | 9.7 | 9.3 | 3.6 | 3.3 | 19.4 | 19.0 |

TABLE II-continued

Elemental Analyses of Products of Examples VII to XII

| Product of | C | | H | | N | | S | |
|---|---|---|---|---|---|---|---|---|
| Example # | Fd. | Calcd. | Fd. | Calcd. | Fd. | Calcd. | Fd. | Calcd. |
| VIII<br>$C_{48}H_{94}N_2S_5$ | 67.0 | 67.1 | 10.6 | 11.0 | 3.2 | 3.3 | 18.9 | 18.6 |
| IX<br>$C_{20}H_{38}N_2S_5$ | 51.1 | 51.5 | 7.9 | 8.2 | 6.4 | 6.0 | 34.6 | 34.3 |

As can be seen from Table II, actual analyses are in quite good agreement with those calculated from structures (1) (below), especially as the products are non-distillable, non-crystallizable oils.

The novel compounds of my invention were synthesized by reacting 0.02 moles each of the products of Examples IV to IX in 50 ml of acetic acid at 30° C. with 4.6 ml (0.044 mole), 6.9 ml (0.066 mole), or 9.2 ml (0.088 mole) of 30% aqueous hydrogen peroxide representing mole ratios of hydrogen peroxide-products of 2:1, 3:1, and 4:1 respectively, by adding the hydrogen peroxide dropwise over 10-30 minutes with stirring, continuing the stirring for 16 hours at 25° C., then evaporating the reaction mixtures in a rotary evaporator at 40° C. and 0.1 to 0.2 Torr. Synthesis of these novel sulfoxides are shown in Table III.

TABLE III

Synthesis of Di-, Tri-, and Tetra-Sulfoxides from Bis-Dithioacetals of 1,3,4-Thiadiazole-2,5-Dithiol

| Example No. | Bis-Thioacetal of Example | Wt., g. | Mole Ratio, Hydrogen Peroxide: Bisthioacetal | Wt. of Sulfoxide Product g, |
|---|---|---|---|---|
| X | IV | 9.32 | 2:1 | 6.97 |
| XI | IV | 9.32 | 3:1 | 8.75 |
| XII | IV | 9.32 | 4:1 | 9.17 |
| XIII | V | 11.56 | 2:1 | 11.95 |
| XIV | V | 11.56 | 4:1 | 12.48 |
| XV | VI | 13.8 | 2:1 | 13.93 |
| XVI | VI | 13.8 | 3:1 | 14.35 |
| XVII | VI | 13.8 | 4:1 | 15.19 |
| XVIII | VII | 16.24 | 2:1 | 15.49 |
| XIX | VII | 16.24 | 4:1 | 15.87 |
| XX | VIII | 16.6 | 2:1 | 16.2 |
| XXI | VIII | 16.6 | 4:1 | 16.64 |
| XXII | IX | 9.32 | 2:1 | 9.74 |
| XXIII | IX | 9.32 | 4:1 | 10.0 |

Elemental analyses of products of Examples X to XXIII are shown in Table IV.

Infrared absorption showed that sulfoxide bands, typically at 1030–1050 cm$^{-1}$, were totally absent in the bis-dithioacetals of Examples IV to IX. The sulfoxide band was present at 1040 cm$^{-1}$ as a strong absorption, becoming stronger with the products of higher molar ratios of hydrogen peroxide to bis-dithioacetal, as shown by the following structures 2, 3, and 4; these have 2, 3, and 4 sulfoxide groups respectively.

The disulfoxides resulting from the reaction of 2 moles of hydrogen peroxide with one mole of bis-thioacetal (1) are written as structure (2), rather than as alternate structures 2a or 2b below:

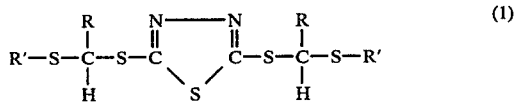

(1)

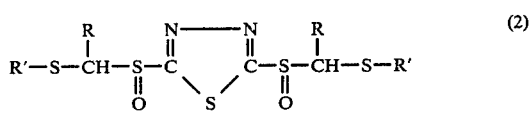

(2)

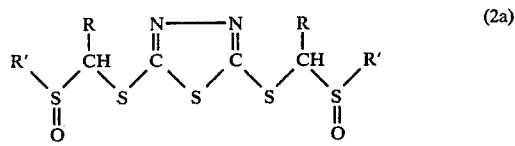

(2a)

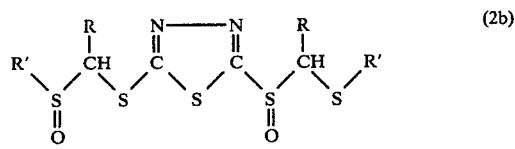

(2b)

Purely aliphatic sulfoxides such as 2a, and mixed alkyl heterocyclic sulfoxides absorb at higher frequencies, about 1050 cm$^{-1}$, whereas heterocyclic and aromatic sulfoxides are lower, 1035–1040 cm$^{-1}$. Further, the $^{13}$C magnetic resonance spectrum shows a peak at 53.55 (TMS) more consistent with

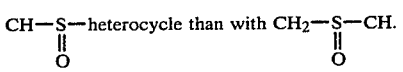

These data strongly support structure 2 for the disulfoxide; however, it is quite possible that some of the disulfoxides present have the structures 2a and 2b, and these are included in these novel polysulfoxides of my invention.

TABLE IV

Elemental Analyses of Products of Examples X to XXIII

| Product of | C | | H | | N | | S | |
|---|---|---|---|---|---|---|---|---|
| Example | Fd. | Calcd. | Fd. | Calcd. | Fd. | Calcd. | Fd. | Calcd. |
| X<br>$C_{20}H_{38}S_5O_2N_2$ | 48.6 | 48.2 | 7.6 | 7.6 | 5.4 | 5.6 | 31.8 | 32.1 |
| XI<br>$C_{20}H_{38}S_5O_3N_2$ | 46.9 | 46.7 | 7.7 | 7.4 | 5.2 | 5.4 | 30.9 | 31.1 |
| XII<br>$C_{20}H_{38}S_5O_4N_2$ | 45.0 | 45.3 | 6.8 | 7.2 | 5.0 | 5.3 | 29.8 | 30.2 |
| XIII<br>$C_{28}H_{54}S_5O_2N_2$ | 55.5 | 55.1 | 9.1 | 8.9 | 4.4 | 4.6 | 26.0 | 26.2 |
| XIV<br>$C_{28}H_{54}S_5O_4N_2$ | 52.2 | 52.3 | 8.6 | 8.4 | 4.2 | 4.4 | 24.6 | 24.9 |

TABLE IV-continued

| | | | | | | | | |
|---|---|---|---|---|---|---|---|---|
| XV $C_{36}H_{70}S_5O_2N_2$ | 60.2 | 59.8 | 10.0 | 9.7 | 3.6 | 3.9 | 22.0 | 22.2 |
| XVI $C_{36}H_{70}S_5O_3N_2$ | 58.0 | 58.5 | 9.9 | 9.5 | 3.6 | 3.8 | 21.4 | 21.7 |
| XVII $C_{36}H_{70}S_5O_4N_2$ | 57.5 | 57.3 | 9.1 | 9.3 | 3.3 | 3.7 | 21.1 | 21.2 |
| XVIII $C_{48}H_{98}S_5O_2N_2$ | 66.4 | 65.9 | 9.1 | 8.9 | 3.0 | 3.2 | 18.1 | 18.3 |
| XIX $C_{48}H_{98}S_5O_4N_2$ | 63.5 | 63.6 | 8.7 | 8.6 | 3.0 | 3.1 | 17.7 | 17.7 |
| XX $C_{48}H_{94}S_5O_2N_2$ | 64.9 | 64.7 | 10.8 | 10.6 | 3.0 | 3.1 | 17.6 | 18.0 |
| XXI $C_{48}H_{94}S_5O_4N_2$ | 63.0 | 62.5 | 10.4 | 10.2 | 2.8 | 3.0 | 17.1 | 17.4 |
| XXII $C_{20}H_{38}S_5O_2N_2$ | 48.4 | 48.2 | 7.8 | 7.6 | 5.3 | 5.6 | 31.9 | 32.1 |
| XXIII $C_{20}H_{38}S_5O_4N_2$ | 45.5 | 45.3 | 7.4 | 7.2 | 5.1 | 5.3 | 29.8 | 30.2 |

Note:
Product names are as follows:

| EXAMPLE | NAME |
|---|---|
| X | 2,5-bis(1-t-octylthiomethylsulfoxy)-1,3,4-thiadiazole |
| XI | 2-(1-t-octylthiomethylsulfoxy)-5-(1-t-octylsulfoxymethyl-sulfoxy)-1,3,4-thiadiazole |
| XII | 2,5-bis(1-t-octylsulfoxymethylsulfoxy)-1,3,4-thiadiazole |
| XIII | 2,5-bis(1-t-dodecylthiomethylsulfoxy)-1,3,4-thiadiazole |
| XIV | 2,5-bis(1-t-dodecylsulfoxymethylsulfoxy)-1,3,4-thiadiazole |
| XV | 2,5-bis(1-t-hexadecylthiomethylsulfoxy)-1,3,4-thiadiazole |
| XVI | 2-(1-t-hexadecylthiomethylsulfoxy)-5-(1-t-hexadecylsulfoxy-methylsulfoxy)-1,3,4-thiadiazole |
| XVII | 2,5-bis(1-t-hexadecylsulfoxymethylsulfoxy)-1,3,4-thiadiazole |
| XVIII | 2,5-bis(1-tert-hexadecylthiomethylphenylsulfoxy)-1,3,4-thiadiazole |
| XIX | 2,5-bis(1-t-hexadecylsulfoxymethylphenylsulfoxy)-1,3,4-thiadiazole |
| XX | 2,5-bis(1-t-hexadecylthio-1-hexylmethylsulfoxy)-1,3,4-thiadiazole |
| XXI | 2,5-bis(1-t-hexadecylsulfoxy-1-hexylmethylsulfoxy)1,3,4-thiadiazole |
| XXII | 2,5-bis(1-octylthiomethylsulfoxy)-1,3,4-thiadiazole |
| XXIII | 2,5-bis(1-octylsulfoxymethylsulfoxy)-1,3,4-thiadiazole |

EXAMPLE XXIV

The following is an example of the use of molecular oxygen and actinic radiation (visible light) in the presence of a dye sensitizer to obtain the bis hydroxy sulfoxides of my invention.

A solution of 15 g (0.1 mole) of 1,3,4-thiadiazole-2,5-dithiol and 23 ml (0.2 mole) styrene in 150 ml of dioxane plus 5 ml of a 0.5% solution of methylene blue in acetone was shaken under oxygen at 23 psig at 20° C. under illumination from a 500 watt lamp for 24 hours. Seventeen pounds oxygen were absorbed. The filtered solution was evaporated in a Rotovapor evaporator at 40° C. and 0.1 Torr to give 47.8 g of viscous yellow product 2,5-bis(β-hydroxy-β-phenylethylsulfoxy)-1,3,4-thiadiazole

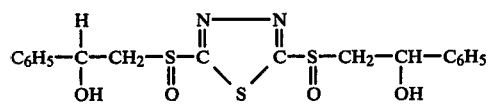

Calcd. for $C_{18}H_{18}N_2O_2S_3$: C, 55.4%; H, 4.6%; N, 7.2%; S, 24.6%. Found: C, 55.4%; H, 4.4%; N, 7.1%; S, 24.8%.

The infrared spectrum showed strong absorption bands for OH at 3300 cm$^{-1}$ and S=O at 1040 cm$^{-1}$, consistent with the structure above.

EXAMPLE XXV

A solution of 7.5 g (0.05 mole) of 1,3,4-thiadiazole-2,5-dithiol, 18 ml (0.1 mole) 1-octene, and 5 ml of 0.5% methylene blue in acetone, in 150 ml of dioxane was shaken under oxygen at 23.5 psig at 25° C. under illumination from a 500 watt lamp for 20 hours. A total of 6.5 lb of oxygen was absorbed. The filter solution was evaporated in a rotary evaporator, ultimately at 40° C. and 0.1 Torr, to obtain 16.3 g viscous light yellow oil, 2,5-bis(β-hydroxyoctyl-4-sulfoxy)-1,3,4-thiadiazole,

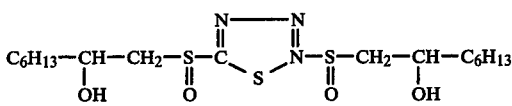

Calcd. for $C_{18}H_{34}S_3O_4N_2$: C, 49.3%; H, 7.8%; N, 6.4%; S, 21.9%. Analysis: C, 48.9%; H, 7.4%; N, 6.1%; S, 21.6%.

EXAMPLE XXVI

A solution of 7.5 g (0.05 mole) of 1,3,4-thiadiazole-2,5-dithiol, 16.8 g (0.1 mole) 1-dodecene, and 5 ml of 0.5% methylene blue in acetone, in 150 ml. of dioxane was shaken under 23.5 psig $O_2$ and illuminated with a 500 watt lamp for 20 hours. 5.5 lb. $O_2$ were absorbed. The filtered solution was evaporated in a rotary evaporator at 40° C. and 0.1 Torr, and gave 23.6 g viscous yellow oil, 2,5-bis(β-hydroxydodecylsulfoxy)-1,3,4-thiadiazole,

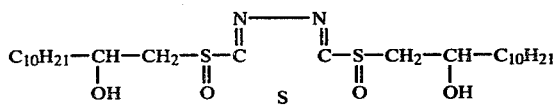

Calculated for $C_{26}H_{50}N_2S_3O_4$: C, 56.7%; H, 9.1%; N, 5.1%; S, 17.9%. Analysis: C, 57.0%; H, 9.1%; N, 4.7%; S, 17.9%.

EXAMPLE XXVII

A mixture of 7.5 g (0.05 moles) of 1,3,4-thiadiazole-2,5-dithiol, 10.5 g (0.1 mole) 4-vinylpyridine, 5 ml. 0.5% of methylene blue in acetone, and 150 ml of dioxane was shaken under 24 psig $O_2$ and illuminated with a 500 watt light bulb for 24 hours. The filtered solution was evaporated in a rotary evaporator at 40° C. and 0.1 Torr to give 19.8 g viscous light brown product, 2,5-bis(β-hydroxy-β,4-pyridylethylsulfoxy)-1,3,4-thiadiazole,

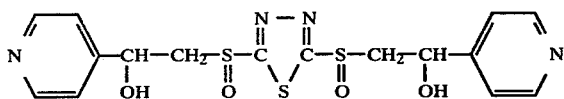

Calculated for $C_{16}H_{16}N_4S_3O_4$: C, 45.3%; H, 3.8%; N, 13.2%; S, 22.6%. Analysis: C, 45.6%; H, 4.1%; N, 12.9%; S, 22.6%.

EXAMPLE XXVIII

The same mixture as in Example XXVII, using 10.5 g of 2-vinylpyridine was treated in the identical fashion and yielded 21.1 g of viscous, light brown product 2,5-bis(β-hydroxy-β,2-pyridylethylsulfoxy)-1,3,4-thiadiazole

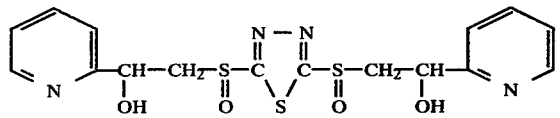

Calculated: C, 45.3%; H, 3.8%; N, 13.2%; S, 22.6%. Analysis: C, 45.7%; H, 4.0%; N, 12.9%; S, 22.3%.

EXAMPLE XXIX

The compounds of this invention are particularly effective rust preventatives for use in steam turbine oils. This is demonstrated by making use of the standard test procedure of the American Society for Testing Materials bearing ASTM designation D-665-60. According to this test procedure, 300 ml of a suitable test oil is placed in contact with 60 ml of distilled or synthetic sea water and the resulting oil-water system is maintained at a temperature of 60° C. for a period of 24 hours with a cylindrical steel specimen completely immersed therein. The specimen is inspected at the end of the period. Within the meaning of this method, a rusted specimen is one on which any rust spot or streak is visible under normal light without magnification.

The polysulfoxides of my invention were tested as rust inhibitors in the ASTM D-665 rust test, at 0.5% concentration by weight. The ratings are based on 10, no rust, clean, to 1 heavy, dark rust. The results are shown below.

| Product, Example No. | Rating |
| --- | --- |
| X | 9 |
| XI | 10 |
| XII | 8 |
| XIII | 10 |
| XIV | 8 |
| XV | 10 |
| XVI | 10 |
| XVII | 9 |
| XVIII | 10 |
| XIX | 10 |
| XX | 9 |
| XXI | 10 |
| XXII | 9 |
| XXIII | 10 |
| XXIV | 10 |
| XXV | 10 |
| XXVI | 10 |

For comparison, the thioacetals of Examples V, VII, and IX gave rust test ratings (0.5% concentration by weight) of 2, 2, and 3, respectively.

EXAMPLE XXX

The compounds were tested as biocides and inhibitors for the growth of micro-organisms by this test: 25 g of agar preparation were placed in standard Petri dishes. The agar preparation consisted of 23.5 g of Bacto Plate Count Agar, Difco Laboratories, Detroit, Michigan, dissolved in 1 liter of water. Plate Count Agar contains a standard USP formula for nutrient agar, consisting of

| | |
| --- | --- |
| 5 g | Pancreatic digest of casein |
| 2.5 g | Yeast extract |
| 1 g | Glucose |
| 15 g | Agar |

Four Petri dishes were untreated and used as blanks. To the others, in duplicate, were added 2.5 ml of 1% acetone solutions of the products of the examples given. All plates were uncovered for 4 hours to expose them to the spores of adventitious fungi and bacteria, then covered and stored at 30° C. for 6 days. Ratings were given at this point; 0 represents no growth, 5 shows luxuriant colonies of fungi and bacteria. Results are shown in Table V.

TABLE V
Biocidal Activity of Polysulfoxides Versus Thiadiazoles and Thioacetals

| Example No. | | Rating | Example No. | Rating |
| --- | --- | --- | --- | --- |
| Control | | 5,5,5,5 | Control | 5,5,5,5 |
| I* | (Thiadiazole) | 2,3 | XIV | 0,0 |
| I | (Polysulfoxide) | 0,0 | XV | 1,1 |
| II* | (Thiadiazole) | 3,4 | XVI | 0,0 |
| II | (Polysulfoxide) | 0,0 | XVII | 0,0 |
| III* | (Thiadiazole) | 3,3 | XVIII | 1,0 |
| III | (Polysulfoxide) | 0,0 | XIX | 0,0 |
| IV* | (Thioacetal) | 2,2 | XX | 1,1 |
| V* | (Thioacetal) | 3,3 | XXI | 1,0 |
| VI* | (Thioacetal) | 1,2 | XXII | 0,0 |
| VII* | (Thioacetal) | 2,3 | XXIII | 0,0 |
| VIII* | (Thioacetal) | 2,2 | XXIV | 0,0 |
| IX* | (Thioacetal) | 3,3 | XXV | 0,1 |
| X | | 0,0 | XXVI | 0,0 |
| XI | | 0,0 | XXVII | 0,0 |
| XII | | 0,0 | XXVIII | 0,0 |

TABLE V-continued

Biocidal Activity of Polysulfoxides Versus Thiadiazoles and Thioacetals

| Example No. | Rating | Example No. | Rating |
|---|---|---|---|
| XIII | 0,0 | | |

*Bis-thiadiazoles of Examples I, II, III and IV are shown separately from polysulfoxides of these same examples. Examples V to IX are thioacetals. Examples X to XXVIII are polysulfoxides.

EXAMPLE XXXI

The original bis-alkylthiothiadiazoles of Examples I and II, thioacetals of Examples III, VII and IX, and the following polysulfoxides were tested as surface-active agents by measuring the interfacial tension between solvent-extracted 5 W oil containing the polysulfoxide against double-distilled water, using a Cenco-Du Nouy Interfacial Tensiometer #70545 with a 6 cm platinum-iridium ring at 25° C., with the results shown in Table VI. The much greater surface activity of the polysulfoxides is demonstrated.

TABLE VI

Surface Activity of Polysulfoxides Versus Thiadiazoles and Thioacetals

| Example No. | | Concentration in 5W Oil, Wt. % | Interfacial Tension Dynes/cm |
|---|---|---|---|
| Control | | — | 34.03 |
| I* | (Thiadiazole) | 0.35 | 31.03* |
| I | (Polysulfoxide) | 0.35 | 10.52 |
| II* | (Thiadiazole) | 1.00 | 24.17* |
| II | (Polysulfoxide) | 1.00 | 4.23 |
| III* | (Thioacetal) | 0.4 | 25.44* |
| VII* | (Thioacetal) | 0.4 | 24.95* |
| IX* | (Thioacetal) | 0.4 | 27.63* |
| X | | 0.32 | 20.32 |
| XI | | 0.04 | 21.15 |
| XII | | 0.02 | 22.03 |
| XIII | | 0.4 | 25.05 |
| XIV | | 0.4 | 20.90 |
| XV | | 0.4 | 19.98 |
| XVI | | 0.4 | 24.62 |
| XVII | | 0.1 | 21.82 |
| XVIII | | 0.4 | 20.32 |
| XIX | | 0.4 | 21.25 |
| XX | | 0.2 | 20.48 |
| XXI | | 0.1 | 18.74 |
| XXII | | 0.25 | 20.16 |
| XXIII | | 0.22 | 20.37 |
| XXIV | | 0.003 | 23.26 |
| XXV | | 0.37 | 14.53 |
| XXVI | | 0.45 | 9.66 |
| XXVII | | 0.05 | 27.06 |
| XXVIII | | 0.1 | 14.53 |

*Bis-thiadiazoles or bis-thioacetals

I claim:

1. A poly sulfoxide selected from the group consisting of: 2,5-bis(1-t-octylthiomethylsulfoxy)-1,3,4-thiadiazole; 2-(1-t-octylthiomethylsulfoxy)-5-(1-t-octylsulfoxymethylsulfoxy)-1,3,4-thiadiazole; 2,5-bis(1-t-octylsulfoxymethylsulfoxy)-1,3,4-thiadiazole; 2,5-bis(1-t-dodecylthiomethylsulfoxy)-1,3,4-thiadiazole; 2,5-bis(1-t-dodecylsulfoxymethylsulfoxy)-1,3,4-thiadiazole; 2,5-bis(1-t-hexadecylthiomethylsulfoxy)-1,3,4-thiadiazole; 2-(1-t-hexadecylthiomethylsulfoxy)-5-(1-t-hexadecylsulfoxymethylsulfoxy)-1,3,4-thiadiazole; 2,5-bis(1-t-hexadecylsulfoxymethylsulfoxy)-1,3,4-thiadiazole; 2,5-bis(1-t-hexadecylthio-1-hexylmethylsulfoxy)-1,3,4-thiadiazole; 2,5-bis(1-t-hexadecylsulfoxy-1-hexylmethylsulfoxy)-1,3,4-thiadiazole; 2,5-bis(1-octylthiomethylsulfoxy)-1,3,4-thiadiazole; 2,5-bis(1-octylsulfoxymethylsulfoxy)-1,3,4-thiadiazole; 2,5-bis($\beta$-hydroxy-$\beta$-phenylethylsulfoxy)-1,3,5-thiadiazole; 2,5-bis($\beta$-hydroxyoctyl-4-sulfoxy)-1,3,4-thiadiazole; 2,5-bis($\beta$-hydroxydodecylsulfoxy)-1,3,4-thiadiazole; 2,5-bis($\beta$-hydroxy-$\beta$,4-pyridylethylsulfoxy)-1,3,4-thiadiazole and 2,5-bis($\beta$-hydroxy-$\beta$,2-pyridylethylsulfoxy)-1,3,4-thiadiazole 2. The poly sulfoxide of claim 1 which comprises 2,5-bis(1-t-octylthiomethylsulfoxy)-1,3,4-thiadiazole.

3. The poly sulfoxide of claim 1 which comprises 2-(1-t-octylthiomethylsulfoxy)-5-(1-t-octylsulfoxymethylsulfoxy)-1,3,4-thiadiazole.

4. The poly sulfoxide of claim 1 which comprises 2,5-bis(1-t-octylsulfoxymethylsulfoxy)-1,3,4-thiadiazole.

5. The poly sulfoxide of claim 1 which comprises 2,5-bis(1-t-dodecylthiomethylsulfoxy)-1,3,4-thiadiazole.

6. The poly sulfoxide of claim 1 which comprises 2,5-bis(1-t-dodecylsulfoxymethylsulfoxy)-1,3,4-thiadiazole.

7. The poly sulfoxide of claim 1 which comprises 2,5-bis(1-t-hexadecylthiomethylsulfoxy)-1,3,4-thiadiazole.

8. The poly sulfoxide of claim 1 which comprises 2-(1-t-hexadecylthiomethylsulfoxy)-5-(1-t-hexadecylsulfoxymethylsulfoxy)-1,3,4-thiadiazole.

9. The poly sulfoxide of claim 1 which comprises 2,5-(bis(1-t-hexadecylsulfoxymethylsulfoxy)-1,3,4-thiadiazole.

10. The poly sulfoxide of claim 1 which comprises 2,5-bis(1-t-hexadecylthio-1-hexylmethylsulfoxy)-1,3,4-thiadiazole.

11. The poly sulfoxide of claim 1 which comprises 2,5-bis(1-t-hexadecylsulfoxy-1-hexylmethylsulfoxy)-1,3,4-thiadiazole.

12. The poly sulfoxide of claim 1 which comprises 2,5-bis(1-octylthiomethylsulfoxy)-1,3,4-thiadiazole.

13. The poly sulfoxide of claim 1 which comprises 2,5-bis(1-octylsulfoxymethylsulfoxy)-1,3,4-thiadiazole.

14. The poly sulfoxide of claim 1 which comprises 2,5-bis($\beta$-hydroxy-$\beta$-phenylethylsulfoxy)-1,3,4-thiadiazole.

15. The poly sulfoxide of claim 1 which comprises 2,5-bis($\beta$-hydroxyoctyl-4-sulfoxy)-1,3,4-thiadiazole.

16. The poly sulfoxide of claim 1 which comprises 2,5-bis($\beta$-hydroxydodecylsulfoxy)-1,3,4-thiadiazole.

17. The poly sulfoxide of claim 1 which comprises 2,5-bis($\beta$-hydroxy-$\beta$,4-pyridylethylsulfoxy)-1,3,4-thiadiazole.

18. The poly sulfoxide of claim 1 which comprises 2,5-bis($\beta$-hydroxy-$\beta$,2-pyridylethylsulfoxy)-1,3,4-thiadiazole.

19. A process for preparing polysulfoxides which comprises the selective oxidation of the reaction product of 1,3,4-thiadiazole-2,5-dithiol (DMTD) and an olefinicaly unsaturated compound wherein the said olefinically unsaturated compound is selected from the group of olefinically unsaturated compounds consisting of styrene, $\alpha$-methylstyrene, $\alpha$-p-dimethylstyrene, allylbenzene, cyclohexene, 1-vinylcyclohexene, ethylene, propylene, 1-butene, 1-octene, 1-dodecene, 1-octadecene, 2-vinylpyridine, 4-vinylpyridine, 2-vinylthiophene, 4-chlorostyrene, 4-nitrostyrene, eugenol methyl ether and 4-dimethylaminostyrene, wherein said DMTD is in the mole ratio to the olefinicaly unsaturated compound of 2:1 to 5:1 at a temperature within the range from about 0° C. to 40° C. with oxygen at 5–200 psig for 0.5 to 150 hours, and actinic radiation in the presence of a dye sensitizer selected from the group consisting of methylene blue, Eosine, and Rose Bengal.

* * * * *

UNITED STATES PATENT OFFICE
CERTIFICATE OF CORRECTION

Patent No. 4,432,847      Dated February 21, 1984

Inventor(s) ELLIS K. FIELDS

It is certified that error appears in the above-identified patent and that said Letters Patent are hereby corrected as shown below:

Column 17, line 68, "5" (first occurence) should be --4--.

Column 18, line 26, "(" (before "bis") should be deleted.

Column 18, line 53, "olefinicaly" should be --olefinically--.

Column 18, line 62, "olefinicaly" should be --olefinically--.

Signed and Sealed this

Thirtieth Day of October 1984

[SEAL]

Attest:

GERALD J. MOSSINGHOFF

Attesting Officer      Commissioner of Patents and Trademarks